(12) United States Patent
Oster et al.

(10) Patent No.: US 9,359,292 B2
(45) Date of Patent: *Jun. 7, 2016

(54) USE OF AN ACETIC ACID/WATER SOLVENT MIXTURE FOR THE PREPARATION OF LOW-SULFATE 5-SULFOISOPHTHALIC ACID, MONO-LITHIUM SALT FROM 5-SULFOISOPHTHALIC ACID

(75) Inventors: Timothy A. Oster, Batesville, AR (US); Michael Todd Coleman, Batesville, AR (US)

(73) Assignee: FutureFuel Chemical Company, Clayton, MO (US)

( * ) Notice: Subject to any disclaimer, the term of this patent is extended or adjusted under 35 U.S.C. 154(b) by 523 days.

This patent is subject to a terminal disclaimer.

(21) Appl. No.: 13/502,333

(22) PCT Filed: Oct. 19, 2010

(86) PCT No.: PCT/US2010/053186
§ 371 (c)(1),
(2), (4) Date: Apr. 16, 2012

(87) PCT Pub. No.: WO2011/049940
PCT Pub. Date: Apr. 28, 2011

(65) Prior Publication Data
US 2012/0245378 A1  Sep. 27, 2012

Related U.S. Application Data

(60) Provisional application No. 61/253,415, filed on Oct. 20, 2009.

(51) Int. Cl.
*C07C 309/00* (2006.01)
*C07C 303/32* (2006.01)

(52) U.S. Cl.
CPC .................................... *C07C 303/32* (2013.01)

(58) Field of Classification Search
None
See application file for complete search history.

(56) References Cited

U.S. PATENT DOCUMENTS

| | | | | |
|---|---|---|---|---|
| 3,594,412 A | * | 7/1971 | Burkhardt | ........................ 562/54 |
| 4,303,577 A | | 12/1981 | Ridgway et al. | |
| 5,777,164 A | | 7/1998 | Boaz | |

(Continued)

FOREIGN PATENT DOCUMENTS

| CN | 1203909 | 1/1999 |
|---|---|---|
| CN | 1673450 | 9/2005 |

(Continued)

OTHER PUBLICATIONS

US Statutory Invention Registration H1760 (Elango, Waradaraj et al.) Nov. 3, 1998.

(Continued)

*Primary Examiner* — Clinton Brooks
(74) *Attorney, Agent, or Firm* — Additon, Higgins & Pendleton, P.A.

(57) ABSTRACT

There is disclosed a process for making a mono-lithium salt of 5-sulfoisophthalic acid (LiSIPA) having less than 200 ppm sulfate. The process uses a reaction mixture of acetic acid, water, a lithium cation producing compound, and 5-sulfoisophthalic acid. The reaction mixture is heated to reflux, cooled, filtered and washed to obtain a high quality LiSIPA having less than 200 ppm sulfate. Also disclosed is a high quality mono-lithium salt of 5-sulfoisophthalic acid having less than 200 ppm sulfate.

12 Claims, 2 Drawing Sheets

(56) References Cited

U.S. PATENT DOCUMENTS

| | | | |
|---|---|---|---|
| 6,133,382 | A | 10/2000 | Studholme |
| 6,334,877 | B1 | 1/2002 | Studholme |
| 6,355,835 | B1 | 3/2002 | Kulsrestha et al. |
| 6,479,619 | B1 | 11/2002 | Duan |
| 6,706,852 | B2 | 3/2004 | Duan et al. |
| 8,178,648 | B2 | 5/2012 | Torno et al. |
| 8,297,035 | B2 | 10/2012 | Chikatsune et al. |
| 8,404,886 | B2 * | 3/2013 | Oster ............................. 562/432 |
| 8,772,522 | B2 * | 7/2014 | Oster ............................... 556/45 |
| 8,809,565 | B2 | 8/2014 | Oster |
| 8,884,045 | B2 * | 11/2014 | Oster et al. ....................... 558/53 |
| 2002/0169273 | A1 | 11/2002 | Duan |
| 2004/0006194 | A1 | 1/2004 | Duan |
| 2004/0242838 | A1 | 12/2004 | Duan |
| 2006/0264665 | A1 | 11/2006 | Gibson et al. |
| 2007/0088133 | A1 | 4/2007 | Heater |
| 2007/0208200 | A1 | 9/2007 | Parker et al. |
| 2009/0054567 | A1 | 2/2009 | Heater |
| 2010/0239512 | A1 | 9/2010 | Morris et al. |
| 2010/0275568 | A1 | 11/2010 | Chikatsune et al. |
| 2012/0225981 | A1 | 9/2012 | Oster |
| 2012/0245378 | A1 | 9/2012 | Oster |
| 2014/0323751 | A1 | 10/2014 | Oster |

FOREIGN PATENT DOCUMENTS

| | | | |
|---|---|---|---|
| CN | 200610043229 | | 8/2006 |
| CN | 101279940 | | 10/2008 |
| CN | 101279940 | A | 10/2008 |
| CS | 119642 | | 8/1966 |
| CS | 157260 | | 12/1973 |
| CS | 162597 | B1 | 7/1975 |
| DE | 19382271 | | 2/1971 |
| IN | 172789 | | 11/1993 |
| IN | WO2009072144 | | 6/2009 |
| JP | 48080539 | | 10/1973 |
| JP | 51004142 | | 1/1976 |
| JP | 1992-247064 | | 9/1992 |
| JP | 2004507604 | A | 3/2004 |
| JP | 2004523630 | A | 8/2004 |
| JP | 2004331527 | | 11/2004 |
| JP | 2005145836 | | 6/2005 |
| JP | 2007063714 | A | 3/2007 |
| JP | 2009510242 | A | 3/2009 |
| WO | WO2011049940 | | 4/2011 |
| WO | 20121054097 | A1 | 4/2012 |
| WO | 2012118973 | A2 | 9/2012 |
| WO | 20121118973 | A1 | 9/2012 |
| WO | 20131025784 | A1 | 2/2013 |
| WO | 20131033022 | A1 | 3/2013 |

OTHER PUBLICATIONS http://www.xuyechem.com/pages/lisipa.htm (Jun. 15, 2008).

Yu, et al., Synthesis of sodium bis(2-hydroxyethyl) 5-sulfoisophthalate, Huaxue Shijie, 2005, pp. 26-29, vol. 46 Issue 1, China.

Zhao, et al, Synthesis of medium-temperature SIPE, Hecheng Xianwei Gongye, 2001, pp. 5-9, vol. 24, Issue 6, China.

Tang, et al., Improvement of the synthetic process of dimethyl 5-sulfoisophthalate sodium salt, Qingdao Keji Daxue Xuebao, Ziran Kexueban 2003, pp. 113-116, vol. 24 Issue 2, China.

Zhang, et al., New Process for the manufacture of dimethyl 5-sulfoisophthalate sodium salt, Jingxi Huagong, 200, pp. 633-636, vol. 17 Issue 11, China.

Zhang, Production technique for dimethyl sodiosulfoisophthalate, Juzhi Gongyye Bianjibu, 2002, pp. 20-22, vol. 15, Issue 1, China.

Wu, et al., Study on the production of dyeing modifer SIPM for polyester fiber, Hecheng Xianwei Gongye, 1995, pp. 11-13, vol. 18, Issue 2, China.

Wu, et al., Synthesis of dyeing improver for cationic dye dyeable polyester fibers, Dalian Ligong Daxue Xuebao, 1995, pp. 434-436, vol. 35 Issue 3, China.

Jiang, et al., Synthesis of sodium 3,5-dimethoxycarbonyl benzene sulfonate, Huagong Shikan, 2000, pp. 21-23, vol. 14, Issue 5, China.

Zhang, et al., Synthesis of sodium 5-sulfodimethylisophthalate, Jingxi Huagong Bianjibu, 1998, pp. 29-41, vol. 15, Issue 3, China.

Li, et al., Synthesis of sodium dimethyl 5-sulfoisophthalate, Jingxi Huangong Bianjibu, 2003, pp. 50-52, vol. 20, Issue 1, China.

Lucas, et al., Substituent dependent dimensionalities in cobalt isophthalate supramolecular complexes and coordination polymers containing dipyridylamine ligands, Inorganica Chimica Acta, 2011, pp. 269-279, vol. 378, Elsevier B.V.

Wu, et al., Synthesis, Structure, and Physical Properties of a Barium Complex with 5-Sulfoisophthalic Acid Sodium Salt, Journal of Inorganic and General Chemistry, 2011, pp. 596-601, vol. 637, Wiley-VCH Verlag GmbH & Co. KGaA, Weinheim, Germany.

Sun, et al., A novel interpenetrating nickel polymer with mixed ligand containing 1D chain and 2D bilayer motifs constructed by 4,4'-bipy, Inorganic Chemistry Communications, 2004, pp. 683-686, vol. 7, Elsevier B.V.

Kim, et al., A thermally stable nanoporous nickel 5-sulfoisophthalate; crystal structure and adsorption properties, ChemComm, 2004, pp. 2148-2149, The Royal Society of Chemistry.

Guo, et al., Synthesis and characterizations of a novel 2-D organic-inorganic hybrid constructed from mixed ligands and mixed-valence copper(I/II), Inorganic Chemistry Communications, 2010, pp. 262-265, vol. 13, Elsevier B.V.

Tao, et al., Hydrothermal Syntheses, Crystal Structures and Photoluminescent Properties of Three Metal-Cluster Based Coordination Polymers Containing Mixed Organic Ligands, European Journal of Inorganic Chemistry, 2004, pp. 125-133, Wiley-VCH Verlag GmbH & Co. KGaA, Weinheim, Germany.

Lin, et al., Poly[(•U2-4,4'-bipyridine)(•u2-3,5-dicarboxybenzenesulfonato)silver(1)], Acta Crystallographica Section E, 2010, pp. m259-m260, vol. E66, CrossMark.

Database Caplus Chemical Abstracts Service, Columbus, Ohio, US; Database Accession No. 1980:585973, Abstract of Harada et al., JP 550334421, 1980.

Nofication of Reasons for Refusal Dispatch No. 339500 for Japanese Patent Application No. 2012-535298, Jun. 24, 2014, Japanese Patent Office.

* cited by examiner

USE OF AN ACETIC ACID/WATER SOLVENT MIXTURE FOR THE PREPARATION OF LOW-SULFATE 5-SULFOISOPHTHALIC ACID, MONO-LITHIUM SALT FROM 5-SULFOISOPHTHALIC ACID

CROSS REFERENCE TO RELATED APPLICATION

The present invention is filed under 35 U.S.C. §371 as the U.S. national phase of International Application No. PCT/US2010/053186, filed 19 Oct. 2010, which designated the U.S. and claims benefit of and priority from prior U.S. Provisional Application 61/253,415 for Use of an Acetic Acid/Water Solvent Mixture for the Preparation of Low-Sulfate 5-Sulfoisophthalic Acid, Mono-Lithium Salt From 5-Sulfoisophthalic Acid, filed 20 Oct. 2009 by Oster et al.

HELD OF THE INVENTION

This disclosure relates to the field of production of salts of derivatives of isophthalic acid. In particular, this disclosure relates to the production of an alkali metal salt, specifically a mono-lithium salt, of 5-sulfoisophthalic acid.

BACKGROUND

This disclosure is intended to teach by way of example and not by way of limitation.

This disclosure relates to the field of preparation of a low-sulfate 5-sulfoisophthalic acid, mono-lithium salt from 5-sulfoisophthalic acid. In particular, this disclosure relates to the preparation of low-sulfate 5-sulfoisophthalic acid, mono-lithium salt (LiSIPA) from 5-sulfoisophthalic acid (SIPA or HSIPA) via the use of an acetic acid/water solvent mixture.

Commercially, LiSIPA is primarily used as an additive in the production of nylon carpet fiber to impart cationic dye-ability to the polymer carpet fiber. The currently utilized processes for the production and purification of LiSIPA have numerous disadvantages, including a low product yield and high manufacturing costs. Further, the resultant LiSIPA from current processes is a LiSIPA with a high sulfate level (i.e., above 200 ppm). More typically the sulfate levels in LiSIPA from known processes are from 1000 to 3000 ppm.

The high sulfate levels are the result of the known manufacturing methods employing a "water-only process" having a product precipitation step utilizing a 30% to 40% sulfuric acid (i.e., sulfate) solution.

A problem inherent to the production of such a high sulfate LiSIPA is the associated high levels of nylon filament breakage due to sulfate precipitation. Accordingly, LiSIPA with a low-sulfate composition is of value because it is expected to reduce the levels of nylon filament breakage due to sulfate precipitation, and reduce the loss of product and throughput that occurs when LiSIPA with higher sulfate levels is used.

Due to these and other problems in the prior art, some of which are disclosed herein, there is now a new process for the preparation of a low sulfate 5-sulfoisophthalic acid, mono-lithium salt from 5-sulfoisophthalic acid via the use of an acetic acid/water solvent mixture.

Liquid acetic acid is a known hydrophilic (i.e., polar) protic solvent, similar to ethanol and water. The moderate relative static permittivity (i.e., dielectric constant) of acetic acid, 6.2, allows it to dissolve not only polar compounds such as inorganic salts and sugars, but also non-polar compounds such as oils and elements such as sulfur and iodine. Acetic acid also has the ability to readily mix with other solvents, both polar and non-polar, such as water, chloroform, and hexane.

Commonly known uses of acetic acid are as a solvent for recrystllization to purify organic compounds. For example, pure acetic acid is used as a solvent in the production of terephthalic acid ("TPA"). Other uses for acetic acid are as a solvent for reactions involving carbocations, such as Friedel-Crafts alkylation and when reducing an aryl nitro-group to an aniline using palladium-on-carbon.

While acetic acid is a known solvent, it is not a solvent that has been utilized in the production and preparation of 5-sulfoisophthalic acid, mono-lithium salt (LiSIPA) or any other salt of 5-sulfoisphthalic acid (HSIPA).

DESCRIPTION OF PREFERRED EMBODIMENT(S)

As used herein, "low sulfate" means a LiSIPA composition containing less than 200 ppm sulfate ($SO_4^{2-}$), as compared to the typical process which results in a LiSIPA composition having sulfate levels in excess of 200 ppm, and more typically in the range of 1000 to 3000 ppm. Furthermore, the low sulfate product of the present invention is the non-purified, direct reaction product of the process. As used herein, the term "non-purified" means that the reaction product that leaves the reaction vessel is not subjected to any further substantive processing or purification steps (other than filtering and washing) to achieve sulfate levels at or below 200 ppm. Specifically, the product of the current invention does not require a LiSIPA re-crystallization-in-water step (which results in low yields due to the high solubility of LiSIPA in water) which is a difficult purification step that is currently used in known processes in an attempt to reduce the sulfate content of LiSIPA.

This process, in its simplified form, comprises: forming a mixture comprising acetic acid, water, a lithium cation producing compound, and 5-sulfoisophthalic acid (HSIPA) and heating this mixture at a sufficient temperature for a sufficient period of time to produce a reaction mixture containing a 5-sulfoisophthalic acid, mono-lithium salt. It should be noted that the order of mixing of the acetic acid, water, lithium cation producing compound, and HSIPA is not critical to the practice of the invention.

Figure 1:
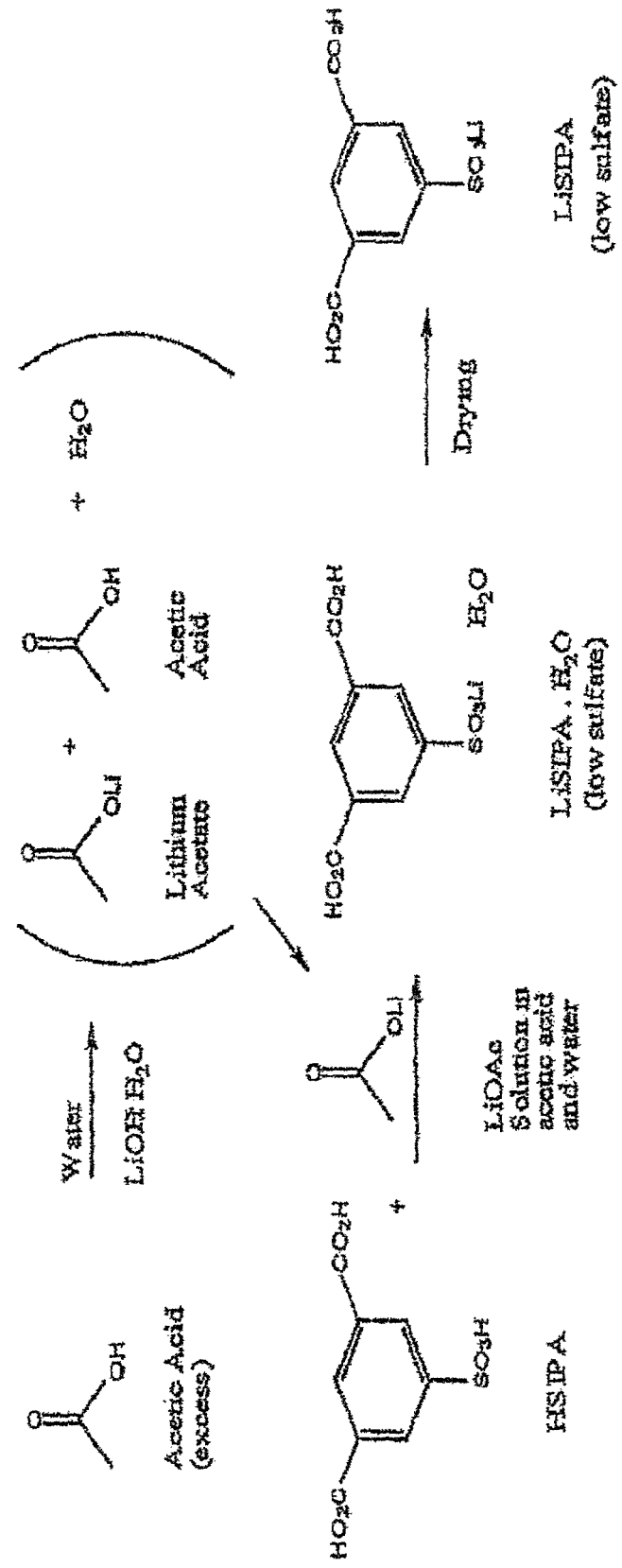
FIG. 1 provides an exemplary flowchart of a process for the preparation of low-sulfate 5-sulfoisophthalic acid, mono-lithium salt from 5-sulfoisophthalic acid via the use of an acetic acid/water solvent mixture.

Turning now to FIG. 1 and preferred embodiments of the invention, in one preferred embodiment the process comprises the addition of a lithium hydroxide monohydrate to a mixture of acetic acid/water to form a solution of lithium acetate, followed by the addition of HSIPA. The mixture is then heated to reflux, held at reflux for a time, then cooled in one or more cooling steps which are held for a time. After refluxing and cooling the reaction mixture containing LiSIPA is filtered to provide a wet cake of low sulfate LiSIPA as a crystalline white solid. A displacement wash of acetic acid is then applied to the cake before drying it in an oven to provide a low-sulfate LiSIPA.

Figure 2:
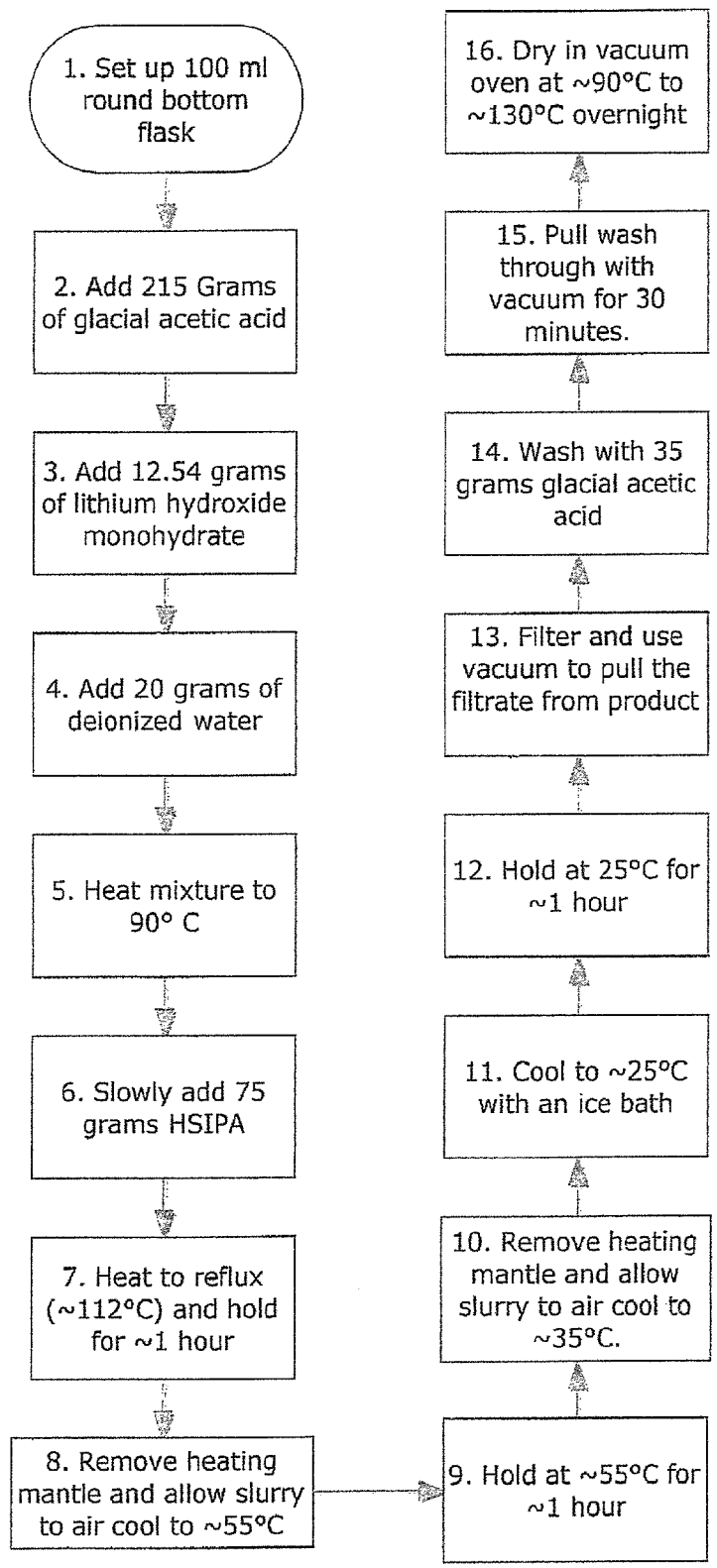
FIG. 2 provides an exemplary flowchart of a numerical step-by-step process for the preparation of low-sulfate 5-sulfoisophthalic acid, mono-lithium salt from 5-sulfoisophthalic acid via the use of an acetic acid/water solvent mixture.

It should be noted that the claimed process for the production of a low-sulfate LiSIPA via an acetic acid/water solvent mixture is a robust process that can be varied in a number of different ways without impacting the resultant product quality. In alternate embodiments, the order of addition of the reactants can be changed. For example, FIG. 2 shows an exemplary process where the lithium cation producing compound (e.g., lithium hydroxide monohydrate) is added to glacial acetic acid prior to mixing with water.

In addition, the specific raw materials of the process can be modified. For example, glacial acetic acid and/or a water-wet acetic acid (such as from a recovery operation), among others, can be used for the "acetic acid" in the process. Preferably the acetic acid used in the process is in excess.

The lithium cation producing compound can be selected from the group comprising lithium hydroxide monohydrate, anhydrous lithium hydroxide, lithium acetate, lithium carbonate or lithium bicarbonate, or other organic or ionic lithium salts. Further, the HSIPA can be anhydrous or as a hydrate or in an aqueous solution; however, when the aqueous solution is used, a distillation is required to remove a portion of the water prior to product isolation for reasons of yield.

Further, the stoichiometry between the lithium cation and the HSIPA can be varied, but in general it is best if the lithium cation is kept as the limiting reagent between 0.95 and 1.0 molar level as compared to HSIPA.

The temperature of the process conditions can be modified, and in some instances, varied substantially. For example, the temperature for the step of mixing the acetic acid, water, lithium cation producing compound, and HSIPA can range from 0° C. to 118° C. (i.e., the boiling point of acetic acid). Similarly, the reflux temperature can vary between 100° C. and 118° C. depending upon the exact makeup of the mixture. In the example of FIG. 2, discussed in more detail below, the reflux temperature was about 112° C. Likewise, the holding time for the reflux step can vary from about 5 minutes to 2 hours or more.

The cooling steps can be varied. The overall goal of the cooling step is to cool the product to a temperature suitable for filtration of the product. Those skilled in the art recognize that this cooling step may be accomplished by any of several known means and that the exact method of cooling will be dictated by the production equipment available to the practitioner. In one preferred embodiment the cooling of the product is a two step process. In the first cooling step the heat source is removed and the product is allowed to air cool to between about 45° C. to about 65° C. where it is held in that range from 1 to 3 hours. A second cooling step comprises cooling the product to between about 0° C. to about 35° C. (i.e., in an ice bath) for about 5 minutes to about 2 hours.

After cooling, the reaction mixture is filtered and washed to recover the product. The filtration step can be any normal method and the wash quantity of the acetic acid can be varied substantially. While the wash can be varied substantially, it should be noted that a small displacement wash is advantageous. Alternate wash solvents are also acceptable depending on the solubility of the product, the interaction with the residual filtrate, and the ease of evaporation. In addition, the drying in the disclosed process can be any method of drying known to those of skill in the art. The product can be isolated as an anhydrous salt or as hydrate, depending on the drying conditions.

As the alternate embodiments of the disclosed process suggest, the process disclosed herein can be readily and easily modified. In fact, it should be noted that it is contemplated that the disclosed process can be modified in any manner known to those of skill in the art that is outside of the disclosed modifications and range changes.

Another exemplary embodiment of the disclosed process is depicted in the flow chart of FIG. 2. As a preliminary matter, it is noted that at any point in this process a sample of the mixture may be taken and submitted for testing using procedures known to those of skill in the art to have utility in such a reaction. In the first step (1) of this embodiment, a 1000 mL round-bottom flask (or similar reaction container equipment known to those of skill in the art) is set up.

Then, in step (2), about 215 grams of glacial acetic acid is added to the flask, followed by about 12.54 grams of lithium hydroxide monohydrate in step (3), and about 20 grams of deionized water in step (4).

Once combined, in step (5), the mixture is heated to about 90° C.

After heating, about 75 grams of HSIPA are slowly added to the mixture in step (6). In one embodiment of this step, the HSIPA used is isolated from a standard plant batch of 5-sulfoisophthalic acid after the water drown step. The analysis of this isolated HSIPA is as follows: Total acidity (NaOH in water)=98.15%; water, % Karl Fisher in pyridine=0.96%; sulfuric acid, % (IC)=0.33%; APHA color=18.

Once the HSIPA is added to the mixture, in step (7) the mixture is slowly heated to reflux (approximately 112°) and held for one hour. Then, in step (8), the heating mantle is removed and the slurry is allowed to air-cool to about 55° C. Once reached, the mixture is held at about 55° C. for one (1) hour in step (9).

After one (1) hour has passed, in step (10) the mixture is removed from the heating mantle and allowed to air-cool until a temperature of around 35° C. is obtained.

Next, once a temperature of around 35° C. is obtained, the mixture is cooled and held at about 25° C. with an ice bath in step (11). Once cooled, in step (12), the mixture is held at about 25° C. for about sixty (60) minutes.

Then, in step (13), the mixture is filtered by any method known to those of skill in the art, and a vacuum is used to pull the filtrate from the product to obtain a cake containing LiSIPA.

After completion of vacuum filtration, in step (14) the mixture is washed with about 35 g glacial acetic acid.

Thereafter, in step (15), the wash is pulled through with a vacuum for thirty (30) minutes. Then, in step (16), the wash-filtrate cake is dried in a vacuum oven at about 90° C. to 130° C. overnight to obtain a low-sulfate LiSIPA.

Also disclosed herein is the product LiSIPA by the claimed process in which acetic acid, water, a lithium cation producing compound, and HSIPA are mixed under conditions sufficient to form low-sulfate LiSIPA.

Also disclosed herein is a 5-sulfoisophthalic acid, monolithium salt composition that contains less than 200 ppm sulfate.

Also disclosed herein is a non-purified reaction product composition of matter consisting essentially of 5-sulfoisophthalic acid, mono-lithium salt having less than 200 ppm sulfate.

There are many advantages to the utilization of an acetic acid/water solvent mixture to prepare low-sulfate LiSIPA. One advantage is that the actual yield based on HSIPA is high as compared to the use of the water-only process of the prior art. Another advantage is that the presence of water in the solvent mixture allows for the use of "water-wet" raw materials (e.g., lithium hydroxide monohydrate, HSIPA monohydrate, water-wet acetic acid from a recovery operation, etc.), thereby allowing LiSIPA to be manufactured at reduced costs as compared to the normally utilized water-only processes. In addition to reducing costs, the production and purification of LiSIPA with an acetic acid/water solvent mixture simplifies the manufacturing process, allowing for the simple recovery of "water-wet" acetic acid solvent via distillation rather than the laborious requirements required in recovering "dry" acetic acid. Further, the crystalline nature of the LiSIPA product that is formed in the acetic acid/water solvent mixture allows for more efficient filtration and washing. Another advantage of the use of the acetic acid/water solvent mixture is the excellent nature of the LiSIPA slurry when the acetic acid/water solvent system is utilized (i.e., a smooth slurry with no stickiness, clumping or reaction with the solvent) that avoids the problems associated with non-polar solvents (e.g., toluene, heptane, etc., can cause sticky, slimy and un-stirrable masses) or alcohols (methanol, ethanol, etc., can partially react to form mono- and di-esters that cause slow filtration and reduce product purity) or water which requires very high solids concentration due to the solubility of LiSIPA, yet still does not reach an acceptable yield because the slurry is too thick. Lastly, the acetic acid/water solvent mixture is able to produce a LiSIPA product with a lower color as compared to processes which utilize ketones (e.g., acetone, MEK, etc.) as the counter-solvent, which allows for the formation of di- and polymeric ketone color bodies.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A process for the preparation of a salt of 5-sulfoisophthalic acid, the method comprising the steps of:
    forming a mixture comprising acetic acid, water, a quantity of a lithium cation producing compound, and a quantity of 5-sulfoisophthalic acid; and
    heating the mixture comprising acetic acid, water, a lithium cation producing compound and 5-sulfoisophthalic acid at a sufficient temperature for a sufficient period of time to produce a mixture containing a 5-sulfoisophthalic acid, mono-lithium salt.

2. A process according to claim 1 wherein said lithium cation producing compound is selected from the group consisting of lithium hydroxide monohydrate, anhydrous lithium hydroxide, organic lithium salts, and inorganic lithium salts.

3. A process according to claim 2 wherein the lithium compound is lithium hydroxide monohydrate.

4. A process according to claim 1 wherein the acetic acid is in excess.

5. A process according to claim 1 wherein the lithium cation is kept as the limiting reagent at a lithium cation to 5-sulfoisophthalic acid molar ratio of 1.0 or less.

6. A process according to claim 1 wherein the mixture comprising acetic acid, water, a lithium cation producing compound, and 5-sulfoisophthalic acid is heated to reflux and held at reflux for a sufficient period of time to produce a mixture containing 5-sulfoisophthalic acid, mono-lithium salt.

7. A process according to claim 1 further comprising the steps of:
    cooling the mixture containing 5-sulfoisophthalic acid, mono-lithium salt;
    filtering the mixture containing 5-sulfoisophthalic acid, mono-lithium salt to obtain a cake containing 5-sulfoisophthalic acid, mono-lithium salt; and
    drying the cake containing a 5-sulfoisophthalic acid, mono-lithium salt.

8. A process according to claim 7 wherein the dried cake containing a 5-sulfoisophthalic acid, mono-lithium salt contains less than 200 ppm sulfate.

9. A process for the preparation of a low-sulfate mono-lithium salt of 5-sulfoisophthalic acid, the method comprising the steps of:
    forming a mixture comprising acetic acid, water, a quantity of a lithium cation producing compound, and a quantity of 5-sulfoisophthalic acid;
    heating the mixture comprising acetic acid, water, a lithium cation producing compound and 5-sulfoisophthalic acid to reflux to produce a mixture containing a 5-sulfoisophthalic acid, mono-lithium salt;
    cooling the mixture containing a 5-sulfoisophthalic acid, mono-lithium salt;
    filtering the mixture containing a 5-sulfoisophthalic acid, mono-lithium salt to obtain a cake containing 5-sulfoisophthalic acid, mono-lithium salt;
    washing the cake containing 5-sulfoisophthalic acid, mono-lithium salt with acetic acid; and
    drying the washed cake containing 5-sulfoisophthalic acid, mono-lithium salt.

10. A process for the preparation of a lithium salt of 5-sulfoisophthalic acid comprising the steps of: (i) forming a cake comprising a lithium salt of 5-sulfoisophthalic acid via an acetic acid/water solvent mixture; and (ii) washing with acetic acid the cake comprising the lithium salt of 5-sulfoisophthalic acid.

11. A process according to claim 10 wherein the step of washing with acetic acid comprises washing with glacial acetic acid.

12. A process according to claim 10 wherein the step of forming a cake comprising a lithium salt of 5-sulfoisophthalic acid via an acetic acid/water solvent mixture comprises:
    forming a mixture comprising acetic acid, water, a quantity of a lithium cation producing compound, and a quantity of 5-sulfoisophthalic acid;
    heating the mixture comprising acetic acid, water, a lithium cation producing compound and 5-sulfoisophthalic acid to reflux to produce a mixture containing a 5-sulfoisophthalic acid, mono-lithium salt;
    cooling the mixture containing a 5-sulfoisophthalic acid, mono-lithium salt; and
    filtering the mixture containing a 5-sulfoisophthalic acid, mono-lithium salt to obtain a cake containing 5-sulfoisophthalic acid, mono-lithium salt.

* * * * *